United States Patent
Nishimoto et al.

[11] Patent Number: 5,941,848
[45] Date of Patent: Aug. 24, 1999

[54] PASSIVE DRUG DELIVERY APPARATUS

[75] Inventors: Fumiaki Nishimoto, Nishinomiya; Kazumasa Maeda, Kadoma; Haruki Kazama, Musashino, all of Japan; Thomas A. Fowles, McHenry, Ill.

[73] Assignee: Baxter International Inc., Deerfield, Ill.

[21] Appl. No.: 08/746,696

[22] Filed: Nov. 14, 1996

[51] Int. Cl.[6] ............................... A61M 37/00
[52] U.S. Cl. ........................................... 604/82
[58] Field of Search ................... 604/82, 83, 85, 604/86, 56, 411–414

[56] References Cited

U.S. PATENT DOCUMENTS

| | | | |
|---|---|---|---|
| 3,868,965 | 3/1975 | Noiles et al. | 604/411 |
| 4,262,671 | 4/1981 | Kersten | 604/411 |
| 4,573,967 | 3/1986 | Hargrove et al. | 604/85 |
| 4,573,993 | 3/1986 | Hoag et al. | 604/411 |
| 4,804,366 | 2/1989 | Zdeb et al. . | |
| 4,822,351 | 4/1989 | Purcell | 604/411 |
| 4,832,690 | 5/1989 | Kuu . | |
| 4,834,744 | 5/1989 | Ritson | 604/411 |
| 4,850,978 | 7/1989 | Dudar et al. . | |
| 4,874,366 | 10/1989 | Zdeb et al. . | |
| 4,936,829 | 6/1990 | Zdeb et al. . | |
| 4,959,053 | 9/1990 | Jang | 604/411 |
| 5,024,657 | 6/1991 | Needham et al. . | |
| 5,049,129 | 9/1991 | Zdeb et al. . | |
| 5,074,844 | 12/1991 | Zdeb et al. . | |
| 5,167,642 | 12/1992 | Fowles . | |
| 5,226,900 | 7/1993 | Bancsi et al. . | |
| 5,334,179 | 8/1994 | Poli et al. | 604/411 |
| 5,356,380 | 10/1994 | Hoekwater et al. . | |
| 5,385,547 | 1/1995 | Wong et al. . | |
| 5,429,614 | 7/1995 | Fowles et al. . | |
| 5,484,406 | 1/1996 | Wong et al. . | |
| 5,547,471 | 8/1996 | Thompson et al. . | |
| 5,656,035 | 8/1997 | Avoy | 604/191 |

FOREIGN PATENT DOCUMENTS 9501133 12/1995 WIPO .
9501196 12/1995 WIPO .

Primary Examiner—John D. Yasko
Assistant Examiner—Manuel Mendez
Attorney, Agent, or Firm—Mark J. Buonaiuto; Jeffrey C. Nichols

[57] ABSTRACT

The present invention provides an apparatus for introducing a reconstituted drug in a drug vial into a medical liquid while venting any gas within the vial to the atmosphere. The assembly includes a receptacle disposed in the middle of a fluid conduit for the medical fluid and which has an upper chamber and lower chamber. The assembly also has a cannula assembly which mounts upon and pierces a septum of the receptacle and also a pierceable stopper of the drug vial. The cannula assembly includes a pair of coaxial cannulas which pierce the stopper of the drug vial and establish a first flow path from the upper chamber to the drug vial and a second flow path from the drug vial to the lower chamber. The cannula assemble also includes a cannula that forms a vent passage in fluid communication with an upper portion of the vial, upon the piercing of the drug vial, with an end of the vent passage communicating with the atmosphere.

4 Claims, 6 Drawing Sheets

PASSIVE DRUG DELIVERY APPARATUS

FIELD OF THE INVENTION

This invention relates to a passive drug delivery apparatus used in conjunction with an administration set in which a beneficial agent is reconstituted through a medical liquid delivered to a patient.

BACKGROUND OF THE INVENTION

Administration sets for intravenously administering a liquid, generally called a transfusion liquid, and sometimes containing a dextrose solution, a solution of salt or water (hereafter called a medical liquid), are widely used. In such a set a particular drug is frequently mixed with the medical liquid to be administered.

The administration set generally comprises a container containing a large volume of medical liquid, a cylindrical instillator, and flow rate control means, a fluid filter, means for removing air, an injection site for injecting additional drug mixture, fluid conduits for connection, and means for coupling inlet and outlet portions.

Conventionally, when the administration set is used to supply a patient with a medical liquid mixed with a particular agent, if the agent is not liquid, it is first liquefied by using a diluent or other agent and then infused into the injection site so that the agent is mixed with the medical liquid.

This method, however, carries a risk of various kinds of contamination that are attributable to the requirements for the work of infusing a drug into the medical solution and preparatory operations therefor.

Various countermeasures have been taken to avoid these risks, and to relieve medical workers from the work.

Representatives of such countermeasures are described in Japanese Patent Publication Nos. 5-60758 and 5-81271. The systems taught by these publications comprises disposing a vial-like drug container in the middle of a fluid conduit for a medical liquid, and passing the medical liquid through the drug container to deliver a mixed solution containing the medical solution and drug. This type of system is referred to as a "passive drug delivery system."

In that system a socket or a receptacle and a cartridge to be coupled therewith are provided. The drug container is attached to the cartridge so that, when the cartridge is connected to the receptacle, the inside space of the drug container is made to communicate with the flow path of the medical solution.

In this passive drug delivery system, once the drug container is docked in the cartridge, there is no chance for the drug in the container to be exposed to the air, and the mixing operation is automatically carried out by the medical solution, so that a very high degree of safety can be secured, and so that the operator's labor can be avoided.

However, in the conventional system it is generally assumed that once the vial has been docked to start the administration, all the administration components should be maintained as they are. Thus, requirements such as enabling rapid administration while keeping the drip speed constant, automatically completing the administration of the entire agent without fear of contamination, and adaptively and smoothly removing or exchanging the used vial, are not necessarily adequately considered.

Therefore the purpose of this invention is to provide an improved passive drug delivery apparatus of a simple structure enjoying the advantages of the passive drug delivery system, wherein normal drug delivery can be rapidly started when necessary, and wherein the interruption of drug delivery, the exchange of a vial, and the complete delivery of the entire drug, can easily be carried out.

SUMMARY OF THE INVENTION

In one aspect of this invention a first flow path is provided introducing into a vial a medical liquid from a fluid conduit for a second flow path is provided for delivering the mixed solution containing the medical liquid and agent from the vial into the fluid conduit. A vent passage is provided for communication of the vial with the atmosphere.

In one preferred embodiment of the present invention, the first flow path for introducing the medical liquid comprises an upper chamber of a receptacle disposed the fluid conduit and an annular space coaxially extending from the upper chamber to an upper part of the vial at around a lower cannula hollow tube which is formed at the lower part of a cannula assembly along the central axis thereof. The cannula assembly extends from the bottom of the vial to a lower chamber of the receptacle when the cannula assembly has piercingly and sealingly been mounted on the receptacle for use. The second flow path for delivering the mixed solution comprises the lower cannula hollow tube extending from an upper part of the vial to the lower chamber of the receptacle and the lower chamber. The vent passage comprises an upper cannula hollow tube which is formed at an upper part of the cannula assembly along the central axis thereof, and which extends from the bottom of the vial to the lower cannula hollow tube. A side cannula hollow tube extends parallel to the lower hollow tube from an end part of the upper cannula hollow tube to a small chamber, which has a vent hole to the atmosphere, and which is intermediately disposed between the vial and the upper chamber. A hollow tube connecting the upper hollow tube and the side hollow tube, and the small chamber.

In another preferred embodiment of this invention, the first flow path for introducing the medical liquid comprises an upper chamber of a receptacle disposed in the fluid conduit and a first toothlike space. The first toothlike space extends around a cannula hollow tube of a cannula assembly from the upper chamber to an upper part of the vial and which is formed at a central part of the cannula assembly extending from the bottom of the vial to a lower chamber of the receptacle when the cannula assembly has piercingly and sealingly been mounted on the receptacle for use. The second flow path for delivering the mixed solution comprises a second space formed around the hollow tube at a central part of the cannula assembly extending from the bottom of the vial to a lower chamber of the receptacle and the lower chamber. The vent passage comprises the cannula hollow tube extending from the bottom of the vial to a small chamber, which is disposed within the lower chamber, and has a vent hole to the atmosphere.

In a further preferred embodiment of this invention, the first flow path for introducing the medical liquid comprises a front chamber of a receptacle disposed in the fluid conduit and a first toothlike space. The first toothlike space extends around a cannula hollow tube of a cannula assembly from the front chamber to an upper part of the vial. The second flow path for delivering the mixed solution comprises the cannula hollow tube extending from the bottom of the vial to a rear chamber of the receptacle and the rear chamber, and the vent passage comprises a second toothlike space, which extends from an upper part of the vial to a small chamber disposed intermediately between the vial and the front chamber, and which is formed around the hollow tube at a central part of the cannula assembly and the small chamber.

In one embodiment of this invention, both a medical liquid inlet provided at an end part of the annular space extending coaxially from the upper chamber to the upper part of the vial and a mixed solution outlet provided at an end part of the lower cannula hollow tube extending from the upper part of the vial to the lower chamber are separated via separate notches provided for their respective flow paths.

DESCRIPTION OF THE PREFERRED EMBODIMENT

Preferred embodiments of this invention will now be detailed by reference to the attached drawings.

Figure 1:
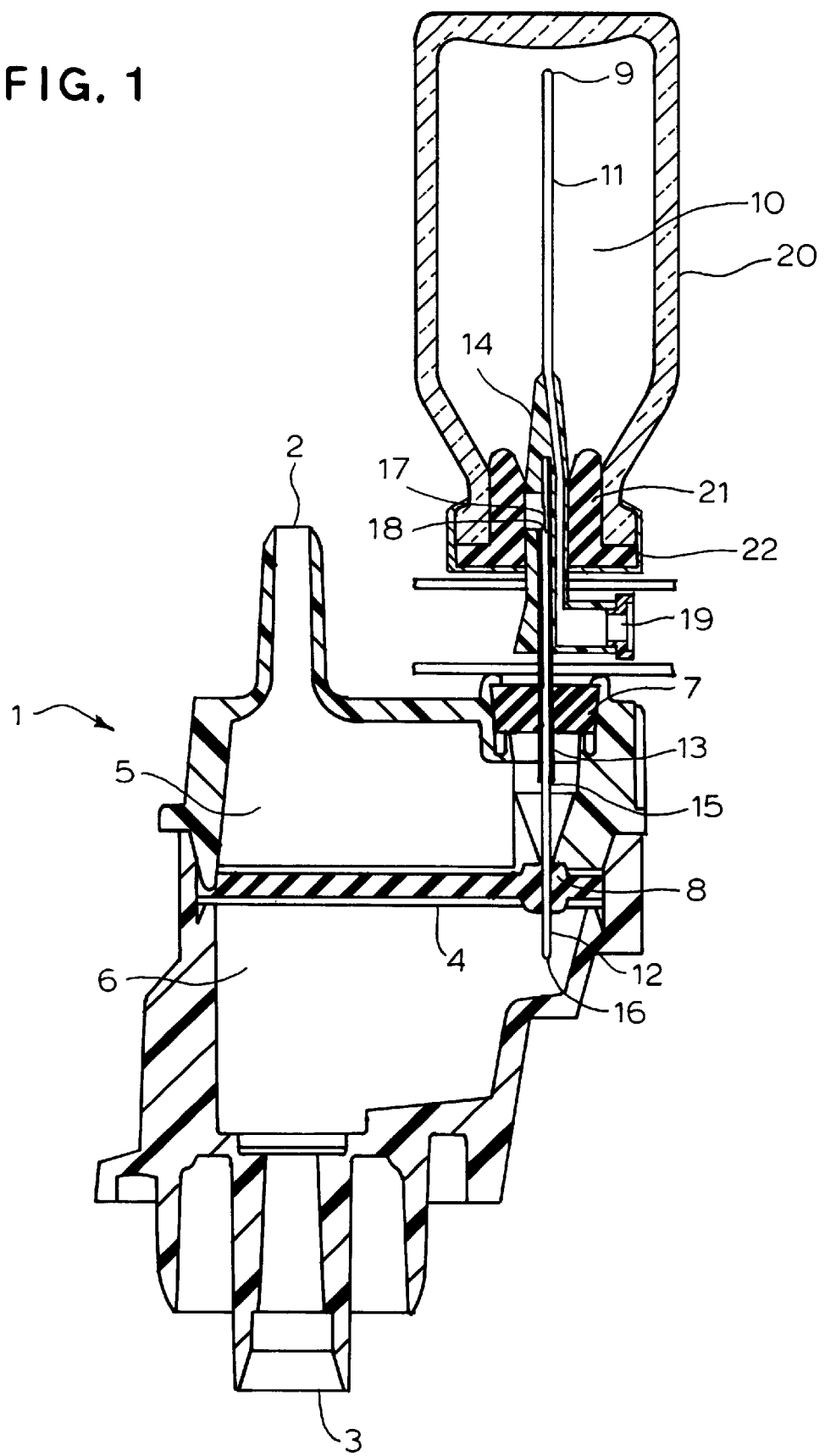
FIG. 1 is an overall schematic diagram showing a first embodiment of the passive drug delivery apparatus of this invention.

FIG. 1 exemplifies an overall schematic of one of the embodiments of the passive drug delivery apparatus of this invention. The apparatus of this invention typically comprises a receptacle 1, a cannula assembly 10, and a vial.

Embodiments

Figure 2:
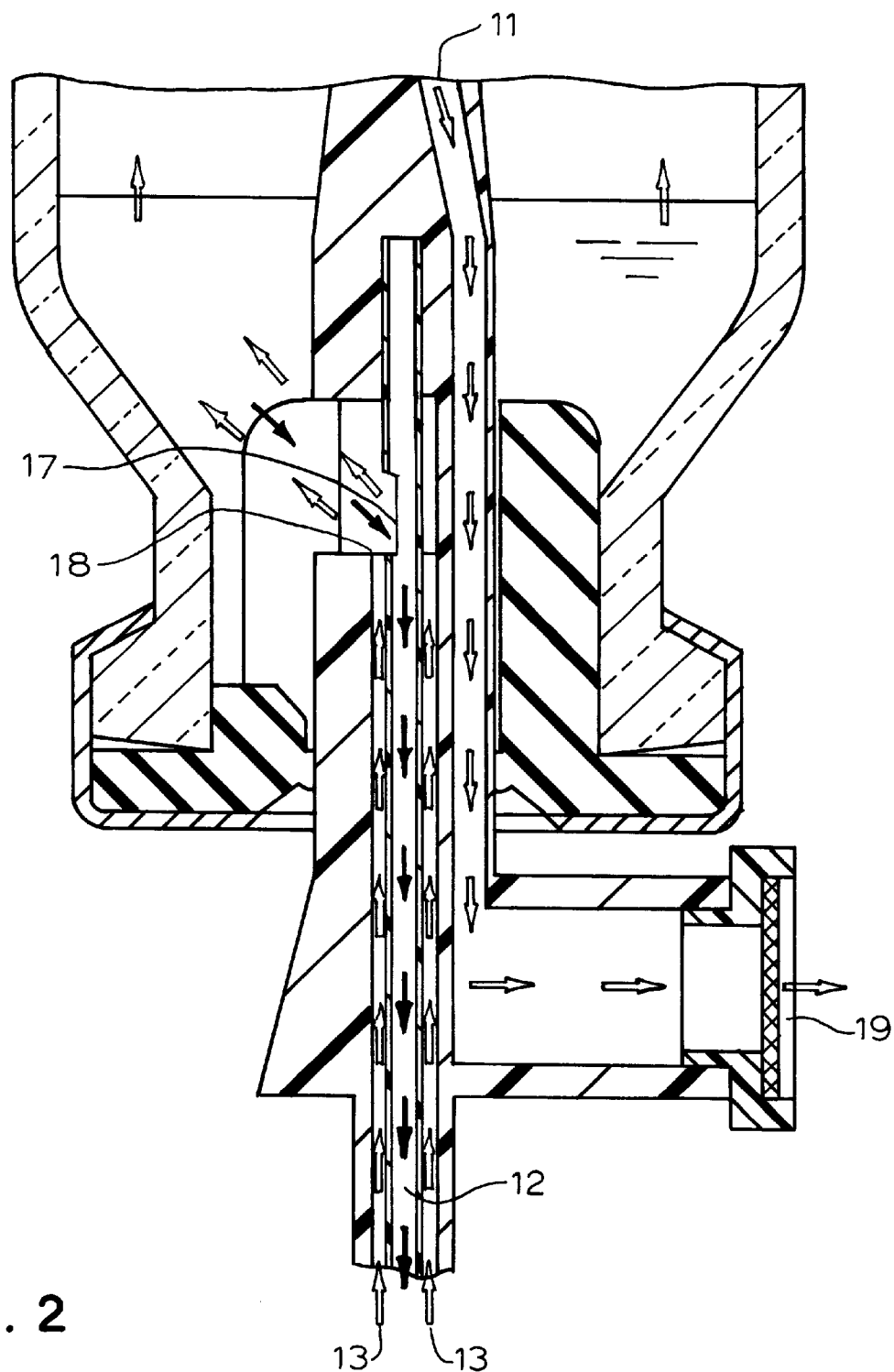
FIG. 2 is a partial and enlarged section of the central part of the cannula assembly of FIG. 1.

In FIGS. 1 and 2, showing a first embodiment of this invention, 1 designates a receptacle or socket connected for use in the middle of a fluid conduit (not shown) to supply a medical liquid. The receptacle 1 communicates via an inlet 2 with an inlet fluid conduit extending to a container for the medical liquid, and also communicates via an outlet 3 with an outlet fluid conduit extending to an intravenous injection member connected to a patient. The recptacle 1 partly constitutes both a flow path for introducing the medical liquid into a vial 20 and a flow path for delivering the mixed solution of an agent in the medical liquid, respectively.

The inner space of the receptacle 1 is divided by a partition wall 4 into an upper chamber 5 and a lower chamber 6, both of which are respectively used for the inlet and outlet flow paths mentioned above. The receptacle 1 has a mount 7 for fixing a cannula assembly 10 at its upper part, and the partition wall 4 has an opening 8 for guiding the lower part of the cannula assembly 10 into the lower chamber 6. Both the situs of the mount 7 and the opening 8 provide a seal with insertions so that the pierceably inserted cannula assembly is sealingly retained.

The cannula assembly 10, extending from the bottom of the vial 20 to the lower chamber 6 after it has pierced, consists of an upper hollow tube 11 functioning as a vent passage and a lower hollow tube 12 functioning as the flow path for delivering the mixed solution. The cannula assembly 10 is structured such that the middle part surrounded by a support 14.

The upper hollow tube 11, having an air inlet 9 at its upper end, extends parallel to the lower hollow tube 12 along the periphery of the support 14, and is connected to an air conduit communicating with a vent hole 19 to the atmosphere. At the middle part of the support 14 the vent hole 19 is provided between the vial 20 and the receptacle 1.

The lower hollow tube 12 has at its lower end an outlet 16 for the mixed solution communicating with the lower chamber 6. The lower hollow tube 12 has at its upper end, an inlet 17 for the mixed solution communicating with the vial 20. An annular space 13 functioning as an inlet for introducing the medical liquid is formed between the lower hollow tube 12 and the support 14 surrounding the periphery of the lower hollow tube. The annular space 13 extends from the lower end of the support 14 to the middle part of the cannula assembly 10. The lower end of the annular space 13 communicates with the upper chamber 5 to function as a medical liquid inlet 15, and the upper end of the annular space 13 communicates with the vial to function as a medical liquid outlet 18.

Figure 3:
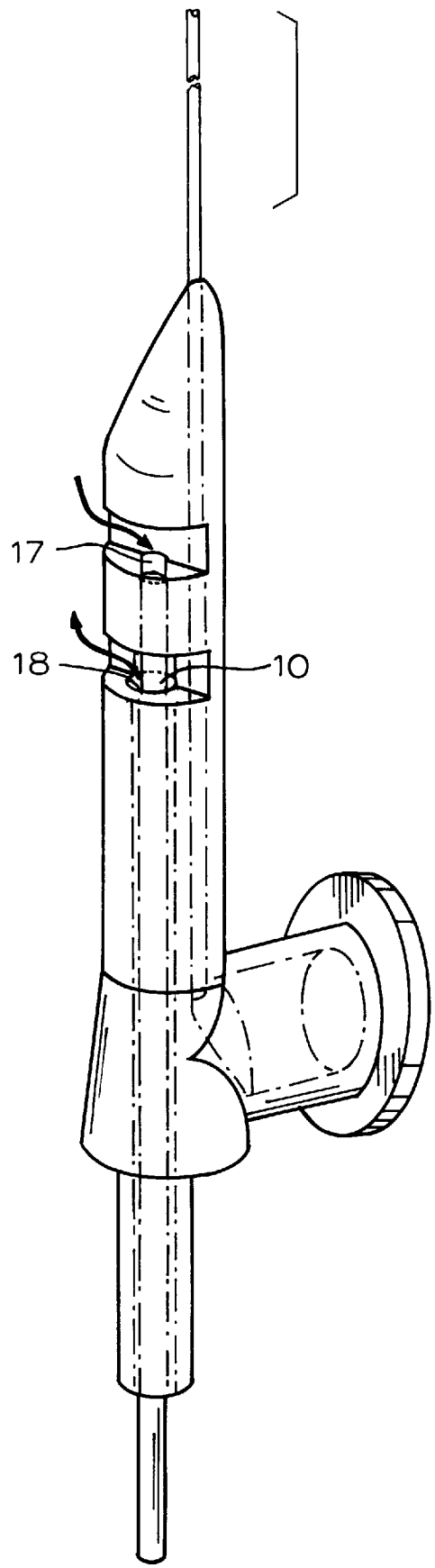
FIG. 3 is a partial section of the cannula assembly of FIG. 1 showing a partial variation.

The overall structure of a variation of the first embodiment of this invention, shown in FIG. 3, is the same as those of FIGS. 1 and 2 except for the structure of a mixed solution inlet 17' and a medical liquid outlet 18' in a cannula assembly 10'. As is clear from the drawing, this variant cannula assembly has respective separate notches to distinctly separate the inlet 17' from the outlet 18' so that interference at the inlet and outlet area between the liquid flowing in both the medical liquid and mixed solution flow paths is completely eliminated. Thus, a more constant and stabilized fluid flow in both the introduction and delivery flow paths is achieved, especially at the beginning and end of the passive drug delivery process.

As can be seen from the above descriptions, the medical liquid introduction flow path consists of the upper chamber 5 and the annular space 13, the drug mixed solution flow path consists of the lower hollow tube 12 and the lower chamber 6, and the vent passage consists of the upper hollow tube and the air conduit having a vent hole 19 to the atmosphere.

Preferably the medical liquid introduction flow path, the drug mixedsolution flow path, and the vent passage, all have smaller dimensions, unless there is a practical hindrance in the delivery operation.

Figure 4:
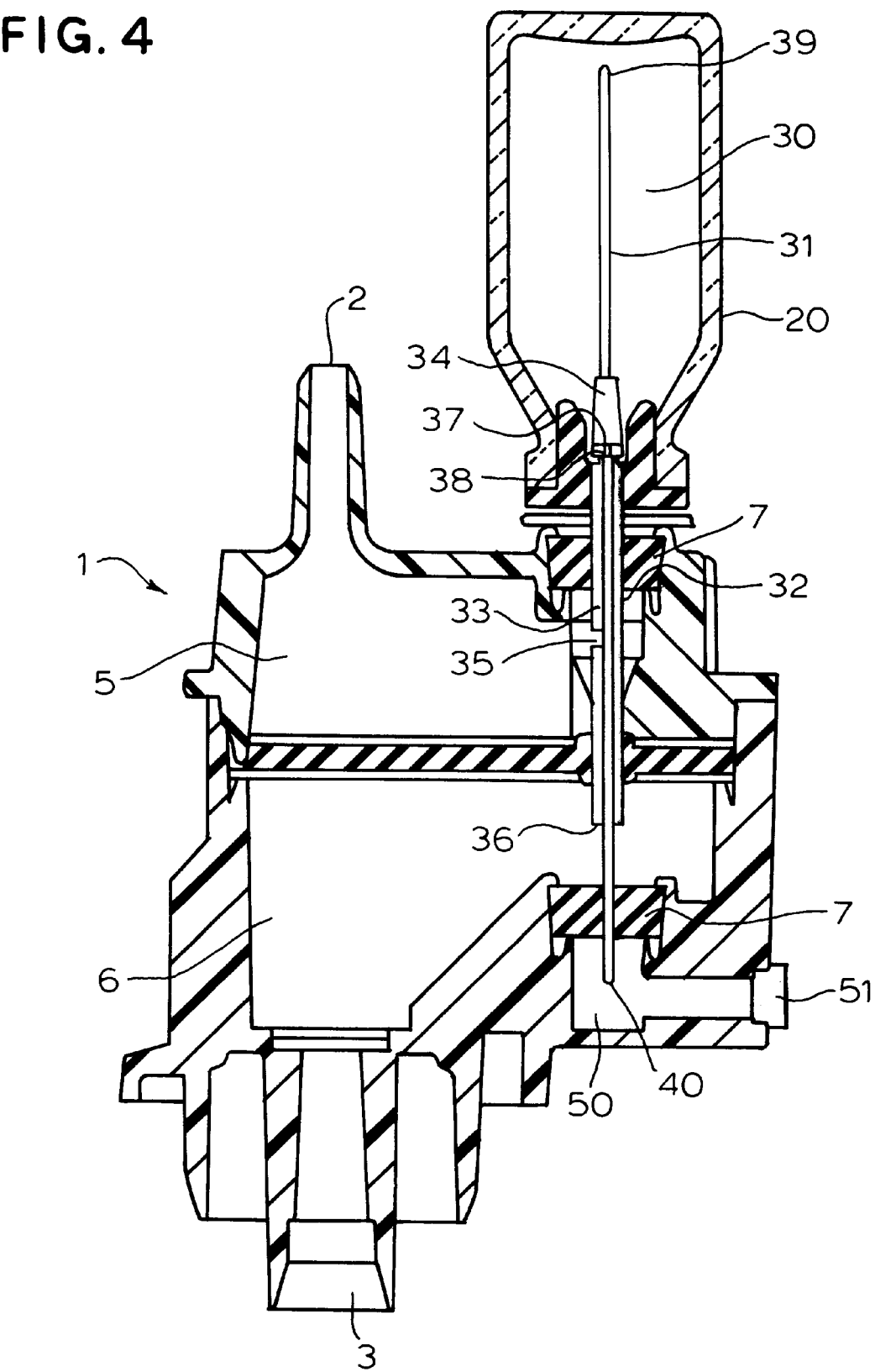
FIG. 4 is an overall schematic diagram showing a second embodiment of the passive drug delivery apparatus of this invention.

A second embodiment made in accordance with the principles of the present invention is shown in FIG. 4, has the same fundamental structure and function as that of FIG.1 except for the constitutions of a cannula assembly 30 and a vent hole 51 to the atmosphere. Below are mainly discussed such structures as are different from those of FIG. 1.

The receptacle 1 has at its upper part a mount 7' to fix the middle part of the cannula assembly 30, and, at its lower part, a mount 7" to fix the lower part of the cannula assembly 30.

The cannula assembly 30 extends from the bottom of the vial 20 to a vent chamber 50 provided at the bottom of the lower chamber 6 when the cannula assembly has been pierceably set for use. The assembly 30 consists of a hollow tube 31 acting as a vent passage, and is surrounded at its middle part by a support 34. The hollow tube 31 has an air inlet 39 at its upper end, and an air outlet 40 at its lower end to form a vent passage through which the air in the vial 20 communicates with the atmosphere via the vent hole 51.

Toothlike spaces 32 and 33, which function respectively as the medical liquid introduction flow path and the drug mixed solution delivery flow path, are formed between the hollow tube 31 and the support 34 surrounding the periphery of the hollow tube. A medical liquid inlet 35 and a medical liquid outlet 37, which communicate respectively with the upper chamber 5 and the vial 20, are provided at the middle and upper parts of the toothlike space 32, respectively. A mixed solution outlet 36 and a mixed solution inlet 38, which communicate respectively with the lower chamber 6 and the vial 20, are provided at the lower end and upper end parts of the toothlike space 33, respectively. Preferably the toothlike spaces 32 and 33 have shapes and structures, as, for example, are detailed in FIG. 5. However, it should be noted that many variations on the toothlike space would be possible for one skilled in the art.

Figure 5:
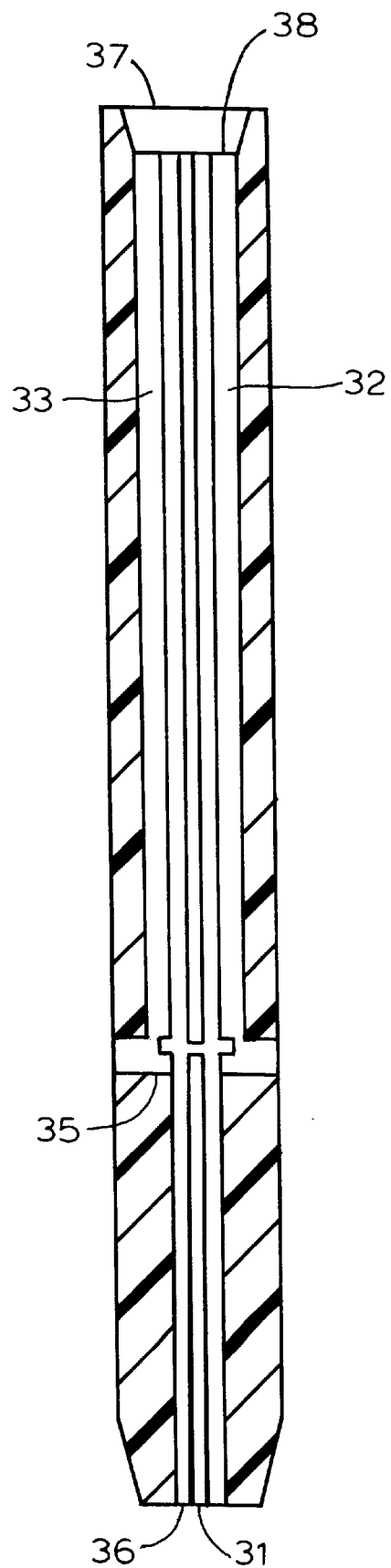
FIG. 5 is a partial and enlarged section of the central part of the cannula assembly of FIG. 4.
Figure 6:
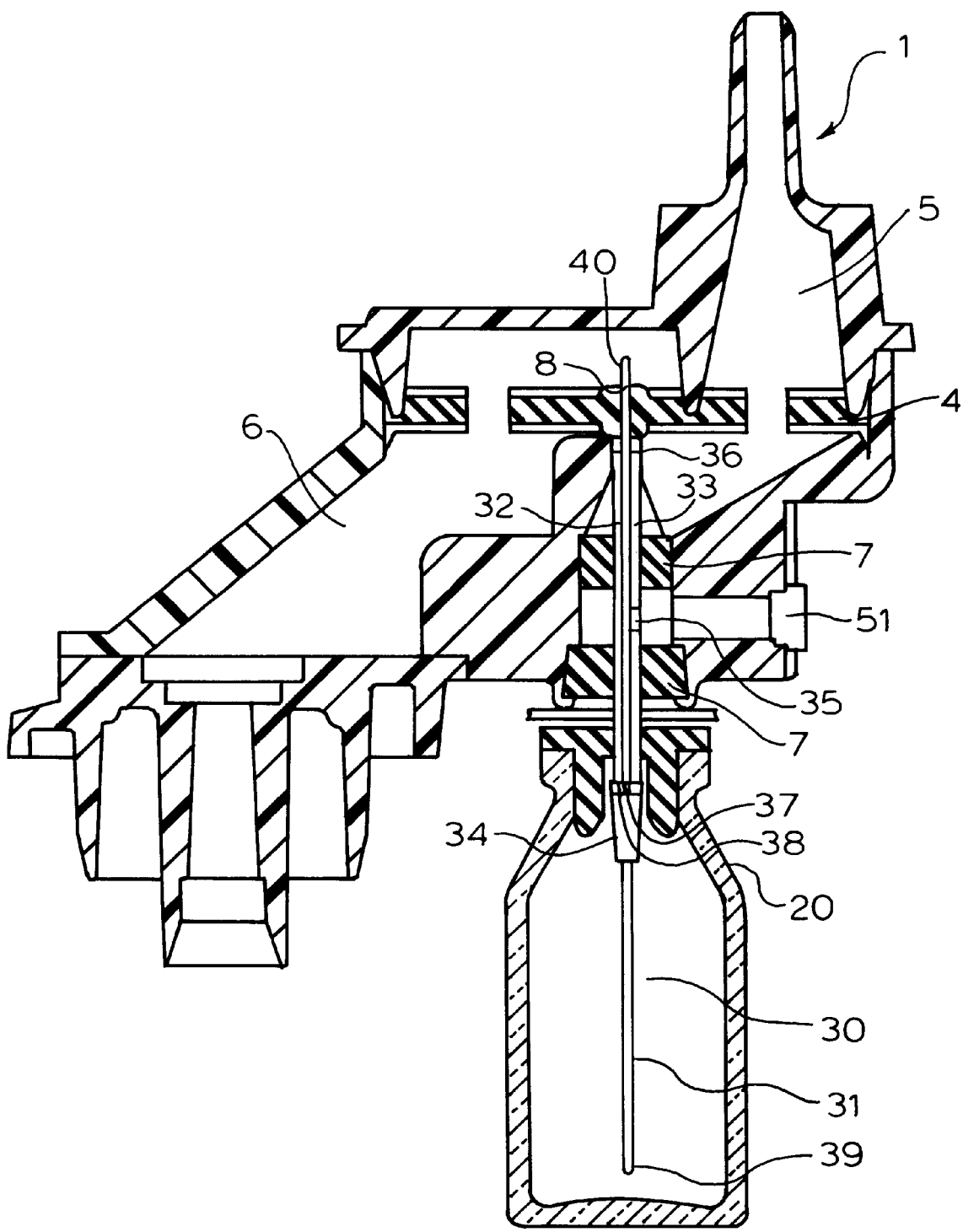
FIG. 6 is an overall schematic diagram showing a third embodiment of the passive drug delivery apparatus of this invention.

A third embodiment of this invention, shown in FIG. 6, has the same fundamental structures and functions as those of FIGS. 4 and 5 except for the functions of the cannula assembly and the receptacle and the positions of the vial 20 and a vent hole 51'. Below are mainly discussed such structures as are different from those of FIGS. 4 and 5.

The space inside the receptacle 1 is divided by a partition wall 4' into a front chamber 5' and a rear chamber 6'. The front and rear chambers form part of the above-mentioned introduction flow path and delivery flow path. The receptacle 1 has mounts 7' and 7" to fix a cannula assembly 30' in the lower part of the front chamber 4'. The partition wall 4' has an opening 8' through which the lower part of the cannula assembly 30' (the upper part in FIG. 6) extends into the rear chamber 6'.

The cannula assembly 30' extends from the rear chamber 6' to the bottom of the vial 20 when it has been pierceably set. The cannula assembly 30' consists of a hollow tube 31' functioning as the drug mixed-solution delivery flow path, and is surrounded by a support 34' at the middle part of the assembly. The hollow tube 31' constitutes the mixed-solution delivery flow path, which has a mixed solution inlet 39' at its upper end and a mixed solution outlet 40' at its lower end, respectively. Toothlike spaces 32' and 33', which function respectively as a vent passage and a medical liquid introduction flow path, are formed between the hollow tube 31' and the support 34' surrounding the periphery of the hollow tube. An air outlet 35' and an air inlet 37', which communicate respectively with an air conduit having a vent hole 51' to the atmosphere and the vial, are provided at the middle and upper end parts of the toothlike space 32, respectively. A medical liquid outlet 38' and a medical liquid inlet 36', which communicate respectively with the vial 20 and the front chamber 5', are provided at the upper end and the lower end of the toothlike space 33', respectively.

The functions of the first, second, and third embodiments of this invention will now be explained by reference to FIGS. 1–6. In all embodiments, when the delivery set is used, the vial 20 is connected to the receptacle 1 through a connecting needle, namely, the cannula assembly 10, 30, which pierces both the vial and receptacle. When the connection is made, when necessary the medical liquid conduit following the drip flask is closed by a clamp, depending upon the volume of the medical liquid container and the purpose of use. However, the apparatus of this invention can be connected without any interruption of the medical liquid supply, resulting in no hindrance.

When in the first and second embodiments the apparatus of the present invention is connected, the medical liquid can more easily be introduced into the vial so that the drug is rapidly dissolved. The reason is that since the vent passage is open to the atmosphere, the difference in head height between the liquid container and the vial, causes the medical liquid to move rapidly. When the vial is filled with the medical liquid up to the air inlet 9, 39, then the vent passage is closed to the atmosphere by the intervening medical liquid. At this point, the medical liquid introduction flow path is completely open. The present invention tends to keep constant the capacity of the overhead space within the drip flask connected to the outlet 3, and causes the mixed solution to be continuously administered to a patient at a given rate. When the mixed solution is administered to the patient and the compressive fluid in the conduit, namely, the air, expands, and the inside pressure is reduced, this negative pressure is automatically canceled through the continuous use of the mixed solution. That is, the steady introduction of the medical liquid to compensate for the consumption of the mixed solution realizes an intended steady drip.

Next the operation of how the purge of the drug, namely, the complete administration or the exchange of the vial (sequential or parallel administration), is carried out. When a large volume of a medical liquid container is used, the purge is started by clamping the conduit between the container and the receptacle. When the drip is continued while the fluid conduit is being clamped, a negative pressure appears in the overhead space. Thus, the mixed solution is delivered to compensate for this pressure, and the mixed solution in the vent passage is returned into the vial so that the vent passage in the vial is placed in open communication with the atmosphere, thereby letting all the mixed solution fall freely. When a small-capacity container is used, the drip can be continued without clamping the fluid conduit in that the similarly-generated negative pressure in the drip flask is compensated for, first by the function of the residual air in the medical fluid container, second by the open communication of the vent passage in the vial with the atmosphere, resulting from progress similar to the above-mentioned one, and finally by the free fall of the mixed solution caused by gravity.

The present of this invention can rapidly start normal drug delivery, interrupt the drug delivery, exchange the vial, and easily purge the entire drug, without sacrificing the advantage of a passive drug delivery system, and without resorting to troublesome manual operations. Therefore, the present invention has practical effects in preventing defects liable to accompany the conventional passive drug delivery system, and thus certainly enhances the usefulness of any passive drug delivery system.

It should be understood that various changes and modifications preferred in to the embodiment described herein will be apparent to those skilled in the art. Such changes and modifications can be made without departing from the spirit and scope of the present invention and without demising its attendance advantages. It is therefore intended that such changes and modifications be covered by the appended claims.

What is claimed is:

1. An apparatus for the delivery of a passively reconstituted beneficial agent contained in a vial into a medical liquid, comprising:

first flow path adapted to introduce into the vial the medical liquid from a fluid conduit, the first flow path including an upper chamber of a receptacle disposed in the fluid conduit and an annular space coaxially extending from the upper chamber to an upper part of the vial at around a lower cannula hollow tube which is formed at the lower part of a cannula assembly along the central axis thereof, the cannula assembly extending from the bottom of the vial to a lower chamber of the receptacle when the cannula assembly has piercingly and sealingly been mounted on the receptacle for use;

second flow path adapted to deliver the mixed solution containing the medical liquid and agent from the vial into the fluid conduit, the second flow path including the lower cannula hollow tube extending from an upper part of the vial to the receptacle lower chamber and the lower chamber; and vent passage means for the communication of the vial with the atmosphere, the vent passage including an upper cannula hollow tube which is formed at an upper part of the cannula assembly along the central axis thereof, and which extends from the bottom of the vial to the lower cannula hollow tube, a side cannula tube extending parallel to the lower hollow tube from an end part of the upper cannula hollow tube to a small chamber, which has a vent hole to the atmosphere, and which is intermittently disposed between the vial and the upper chamber, a hollow tube connecting the upper hollow tube and the side hollow tube, and the small chamber.

2. The apparatus of claim 1, wherein both a medical liquid inlet provided at an end part of the annual space extending coaxially from the upper chamber to the upper part of the vial and a mixed outlet provided at an end part of the lower cannula hollow tube extending from the upper part of the vial to the lower chamber are set apart by separate notches provided for their respective flow paths.

3. An apparatus for the delivery of a passively reconstituted beneficial agent contained in a vial into a medical liquid, comprising:

first flow path adapted to introduce into the vial the medical liquid from a fluid conduit, the first flow path including an upper chamber of a receptacle disposed in the fluid conduit and a first toothlike space, which extends around a cannula hollow tube of a cannula assembly from the upper chamber to an upper part of the vial, and which is formed at a central part of the cannula assembly extending from the bottom of the vial to a lower chamber of the receptacle when the cannula assembly has piercingly and sealingly been mounted on the receptacle for use;

second flow path adapted to deliver the mixed solution containing the medical liquid and agent from the vial into the fluid conduit, the second flow path comprises a second space formed around the hollow tube at a central part of the cannula assembly extending from the bottom of the vial to a lower chamber of the receptacle and the lower chamber; and vent passage means for the communication of the vial with the atmosphere, the vent passage means including the cannula hollow tube extending from the bottom of the vial to a small chamber, which is disposed within the lower chamber, and has a vent hole to atmosphere.

4. An apparatus for the delivery of a passively reconstituted beneficial agent contained in a vial into a medical liquid, comprising:

first flow path adapted to introduce into the vial the medical liquid from a fluid conduit, the first flow path including a front chamber of a receptacle disposed in the fluid conduit and a first toothlike space, which extends around a cannula hollow tube of a cannula assembly from the front chamber to an upper part of the vial;

second flow path adapted to deliver the mixed solution containing the medical liquid and agent from the vial into the fluid conduit, the second flow path including the cannula hollow tube extending from the bottom of the vial to a rear chamber of the receptacle and the rear chamber; and vent passage means for the communication of the vial with the atmosphere, the vent passage means including the second toothlike space, which extends from an upper part of the vial to a small chamber disposed intermediately between the vial and the front chamber, and which is formed around the hollow tube at a central part of the cannula assembly and the small chamber.

* * * * *

UNITED STATES PATENT AND TRADEMARK OFFICE
CERTIFICATE OF CORRECTION

PATENT NO. : 5,941,848
DATED : August 24, 1999
INVENTOR(S) : Nishimoto et al.

It is certified that error appears in the above-identified patent and that said Letters Patent is hereby corrected as shown below:

Title page item [73], Assignee, line 2, insert --Kanae Co., Ltd., Osaka, Japan--

Signed and Sealed this

Fifteenth Day of August, 2000

Attest:

Q. TODD DICKINSON

Attesting Officer        Director of Patents and Trademarks